(12) United States Patent
Corrêa Bittencourt et al.

(10) Patent No.: US 8,965,186 B2
(45) Date of Patent: Feb. 24, 2015

(54) DEVICE WITH HEATING AND TEMPERATURE MONITORING SYSTEM OF FLUID IN SINGLE AND MULTIPLE CONTAINER SETS FOR PARENTHERAL SOLUTIONS

(76) Inventors: João Bosco Corrêa Bittencourt, Goiânia (BR); José Eduardo Alves Pereira, Goiânia (BR)

( * ) Notice: Subject to any disclaimer, the term of this patent is extended or adjusted under 35 U.S.C. 154(b) by 0 days.

(21) Appl. No.: 10/570,187

(22) PCT Filed: Aug. 10, 2004

(86) PCT No.: PCT/BR2004/000147
§ 371 (c)(1),
(2), (4) Date: Feb. 28, 2006

(87) PCT Pub. No.: WO2005/022097
PCT Pub. Date: Mar. 10, 2005

(65) Prior Publication Data
US 2007/0007277 A1   Jan. 11, 2007

(30) Foreign Application Priority Data

Aug. 28, 2003  (BR) .................................. 03047377

(51) Int. Cl.
*A61F 7/00*    (2006.01)
*A61M 5/44*   (2006.01)
*A61J 1/16*    (2006.01)

(52) U.S. Cl.
CPC ............... *A61J 1/16* (2013.01); *A61J 2200/42* (2013.01)
USPC ........................................... 392/470; 604/113

(58) Field of Classification Search
USPC ........................................... 392/470; 604/113
See application file for complete search history.

(56) References Cited

U.S. PATENT DOCUMENTS

| | | | |
|---|---|---|---|
| 4,878,537 A * | 11/1989 | Verkaart ....................... | 165/156 |
| 4,934,336 A * | 6/1990 | White ....................... | 126/263.01 |
| 5,254,094 A * | 10/1993 | Starkey et al. ................ | 604/113 |
| 5,601,894 A * | 2/1997 | Maruschak ................... | 428/36.9 |
| 6,236,809 B1 * | 5/2001 | Cassidy et al. ................ | 392/470 |
| 6,315,759 B1 * | 11/2001 | Peterson ....................... | 604/171 |
| 6,641,556 B1 * | 11/2003 | Shigezawa .................... | 604/113 |
| 6,746,439 B2 * | 6/2004 | Lenker ........................ | 604/500 |
| 6,746,440 B2 * | 6/2004 | Magnusson et al. .......... | 604/500 |
| 6,824,528 B1 * | 11/2004 | Faries et al. .................. | 604/113 |

* cited by examiner

*Primary Examiner* — Thor Campbell
(74) *Attorney, Agent, or Firm* — B. Aaron Schulman, Esq.; Stites & Harbison, PLLC

(57) ABSTRACT

The invention is a device that consists of an assemblage of shielded resistors and temperature monitoring sensors. The managing of these functions is effected by central control unit, which receives electricity and converts it to a 40 to 60 Volt band thus feeding the resistors and controlling the chosen temperature through sensors included in the device.

5 Claims, 7 Drawing Sheets

DEVICE WITH HEATING AND TEMPERATURE MONITORING SYSTEM OF FLUID IN SINGLE AND MULTIPLE CONTAINER SETS FOR PARENTHERAL SOLUTIONS

BACKGROUND OF INVENTION

The present invention refers to a device including a heating and temperature monitoring systems of fluid for parenteral feeding with the aim of keeping the temperature of the fluid to be administered to patients being examined, clinically or surgically treated, etc.

SUMMARY

This device consists of an assemblage of shielded resistors and temperature monitoring sensors. The managing of these functions is effected by central control unit, which receives electricity and converts it to a 40 to 60 Volt band thus feeding the resistors and controlling the chosen temperature through sensors included in the device.

The ministering of fluids to patients is of vital importance in several medical proceedings, clinical or surgical, ministered in private practices, hospitals, labs, etc.

In surgical proceedings executed in hospitals, there are norms and technical criterions for keeping the patient's temperature.

Especially in pre, trans and post-operatory phases, one should keep the patient's temperature close to normal physiological temperature so as to avoid hypothermia and its various consequences, among them delay in anesthesia recovering, increase of oxygen demand, which causes hypoxemia due to muscular trembling, etc.

Taking all this into account, several proceedings are used to heat up the fluid used in parenteral feeding so as to level the fluid's temperature to the physiological temperature of the patient. Among these various proceedings one finds microwave heating, double-boiling over a stove and immersion.

There are several disadvantages in the above-mentioned proceedings utilized nowadays. The main one is the lack of exact control over the temperature of the fluids to be ministered to the patients, involving the chance of blood hemolysis, electrochemical changes in the several parenthetic solutions used, even the caramelizing of fluids and solutions containing glucose, etc.

All these possibilities are due to the lack of control over the heating temperature of hospital solutions when one resorts to heating procedures such as double-boiling or immersion. It is virtually impossible to control the temperature of the heated fluid and this is even true of microwave ovens, since the effectiveness of the heating may vary a lot due to variations on the thickness and size of the package in which the fluid is stored, the oven's power, heating time, etc. It was in view of the above disadvantages and difficulties that we have developed the current invention. It is a device that allows the storage of single and multiple containers with several hospital fluids and solutions, keeping them in a stable pre-established temperature through constant monitoring of the temperature by sensors and a automatic system controlled by thermostat and digital displays which easily allow the control and maintenance of the temperature of the stored fluids. This is achieved both for the solutions nowadays being fed to the patients as well as for the ones stored within the system for ulterior usage.

The main advantages in the use of the current invention are, first of all, to maintain the desired temperature of parenteral solutions close to the physiological temperature, thus avoiding patient temperature change such as hypothermia, Besides that, it also prevents electrochemical change in the various kinds of compounds present in parenthetical solutions fed to patients for food requirement of medical treatment.

BRIEF DESCRIPTION OF DRAWINGS

The current invention will be much better understood by the following detailed description in accordance with the figures attached, where.

DETAILED DESCRIPTION

Figure 1:
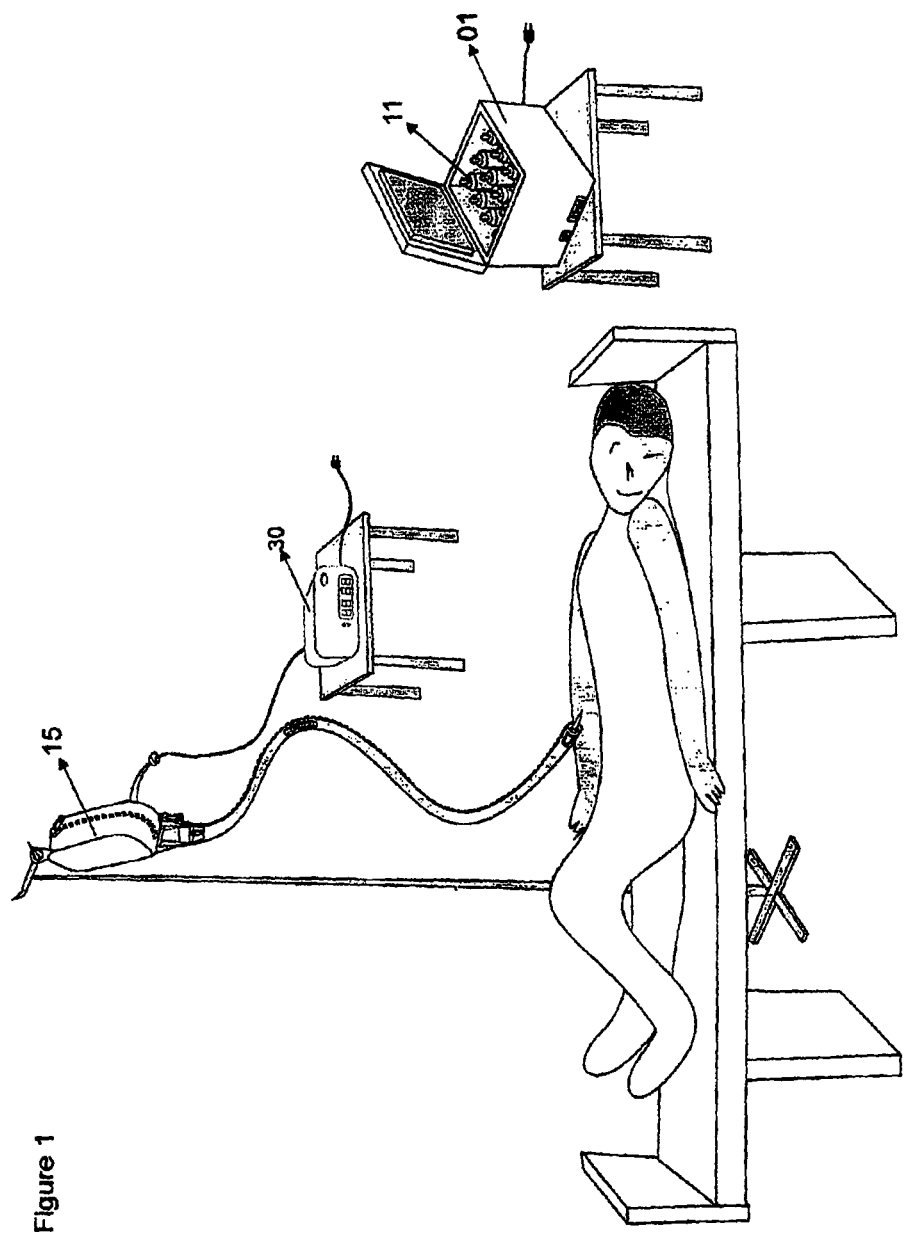
FIG. 1 represents the device with the heating and temperature monitoring systems being used on a patient on a hospital's bed.
Figure 2:
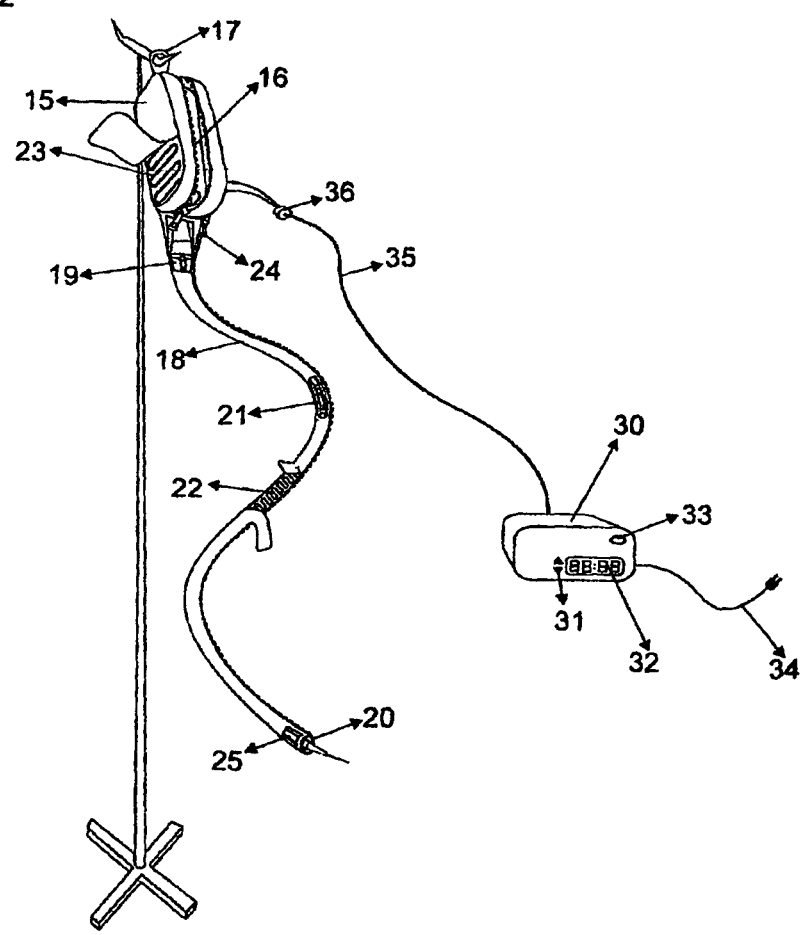
FIG. 2 shows the device with heating and temperature monitoring systems in such a way that it allows the heating of an individual parenteral solution's container, all the way from the main reservoir to the tip of the needle at the other end of the patient's catheter.
Figure 3:
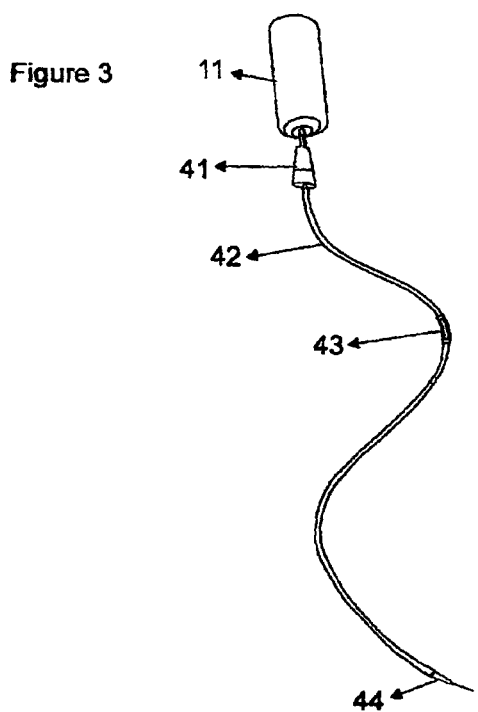
FIG. 3 represents a frontal view of a certain fluid solution's set including a solution's container and the IV device (fluid tube).
Figure 4:
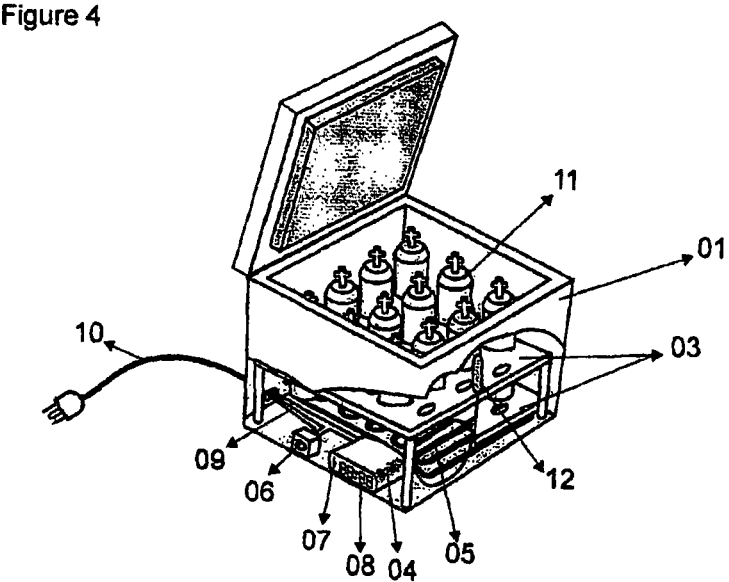
FIG. 4 represents a lateral view in perspective of the device with heating and temperature monitoring systems, with a lateral inside view of the heating and monitoring devices. The figure shows several ready to use stored containers, all of which within a fixed desired temperature.
Figure 5:
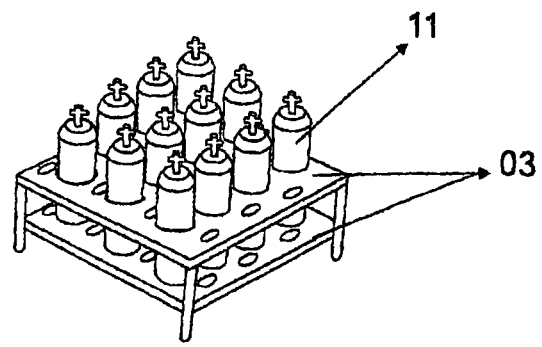
FIG. 5 represents a lateral view in perspective of the supporting frame for holding and storing the containers or packages of fluid.
Figure 6:
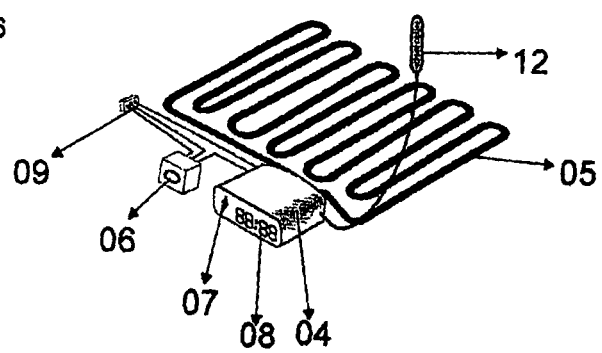
FIG. 6 represents a lateral view in perspective of the whole heating and temperature monitoring devices of the thermal box where the containers are to be stored.
Figure 7:
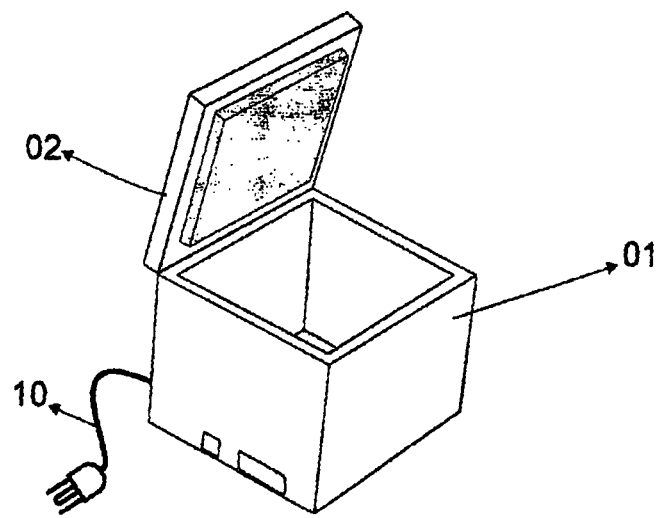
FIG. 7 represents in perspective a lateral view of the thermal Box, which is included as part of the set, together with the heating and temperature monitoring systems.

In those figures we can see that:

The device with heating and temperature monitoring systems includes a thermally protected storage Box (01), with a also thermally protected lid (02), and a supporting frame (03) for holding and storing the containers or packages of parenteral solutions.

The Thermal Box (01) is equipped with a Central control unit (04) consisting of a totally independent power supply unit that converts public electrical supply to a 40 to 60 volt range feeding the shielded Resistors (05), which internally heat up the Thermal Box (01). This whole system is operated by an on/off key (06). The Central control unit (04) is also, equipped with programming Buttons (07), which allow the setting of the desired temperature. This temperature can be checked in the digital Display (08) located on the outside front of the central control unit (04).

This unit monitors the internal temperature through a temperature Sensor (12), a device activates the Central thermostat control unit (04), turning it on or off whenever inside temperature is not leveled with the one programmed in the Controller (07).

The electrical supply for the Central control unit (04) derives from the Power supply unit (09), which is thermally shielded from the electrical network and is electrically fed by the Power cable (10).

The storage Box with its thermal shield (01) is integral part of the current invention and is used to store and keep the parenteral solutions' containers or packages (11) within a set temperature, so that these solutions may always be in ideal temperature for usage with patients.

With this goal in view, the current invention is also equipped with a Heating Bag (15), which is used together with the individual container for storing and keeping the preprogrammed temperature of the individual container or package (11) with the solution to be fed to the patient.

This Heating Bag (15) is equipped with: a Zipper (16) for closure and internal protection; an electrically shielded Resistor (23), which heats it up; the Bag (15) includes a Hooker (17) for hanging it on appropriate resting-places; and also a protracted thermal Bag (18) for heating and keeping the temperature of the solution within the Catheter (42) all way down to the patient.

This protracted thermal Bag (18) is equipped all along with a thermally shielded Resistor (22), of course; with a transparent Display (19), which allows visualization of the dripping reservoir's Cup (41); as well as the Opening (21), which allows the control of solution's flow rate through the Regulator (43). The protracted thermal Bag (18) is directly set on along the Catheter (42) of the IV device so as to heat up and maintain the solution's temperature all its way down to the needle. This protracted Thermal Bag (18) also has a Zipper (24) running all along, allowing its removal and fastening for easy storage of the IV device for parenteral feeding. It also has a transparent Display (25) next to the tip of the Catheter (42) allowing visual control of the solution's exiting rate and so checking the final feeding of the parenteral solution to the patient through the needle (44).

The protracted Thermal Bag (18) also has a temperature Sensor (20) set next to the end of the Catheter (42) so as to allow monitoring of the temperature at the very tip of the duct and consequently allowing possible readjustments.

Both the Heating Bag (15) and the protracted thermal Bag (18) are electrically fed by the externally placed Central control unit (30). This unit includes a power supply unit, which creates an independent internal electrical network and converts the electrical supply into a 40 to 60 volt range. The unit feeds the electrical resistors (23 and 22) that heat up the Heating Bag (15) and the Protracted Thermal Bag (18). The system is operated by an on/off Key (33).

The Central control unit (30) also includes Programming Buttons (31) for adjustment of the desired temperature, which can be checked in the digital Display (32).

The electrical supply is done by the power Cable (34) connected to the Central control unit (30), which, by way of the Cable (35), feeds converted electrical power to the electrical Resistors (22 and 23) and to the temperature Sensor (20), which in its turn monitors the solution's temperature in the Catheter (42) inside of the Protracted Thermal Bag (18).

The proposed system is thus highly effective in heating and monitoring the temperature of the most diverse parenteral solutions used in human and in veterinarian treatment. It allows the heating and temperature monitoring either of a single container or package or even set of several packages together, keeping them all in an ideal temperature for medical proceedings.

It goes without saying that such practical and efficient device could be manufactured so as to be able to store and heat up the most diverse sizes and models of solutions' packages known today or even future ones.

The invention claimed is:

1. A device for heating and monitoring of parenteral fluids comprising:
   (a) a container having heating and temperature monitoring systems of fluid in single and multiple container sets for parenteral fluids, said container storing bottles, or packages of intravenous solution by units in a heated pouch equipped with a sealing device and sealed conductor linked by an electric connector, and said container providing temperature monitoring of the intravenous solution while the intravenous solution is being administered to the patient through a needle directly from an exit tip of a catheter extending from said container to the patient and having a temperature sensor,
   (b) a protracted thermal bag that covers said catheter for heating and maintaining the temperature of the intravenous solution from the container to the patient;
   (c) a visualizing dripping cup and a regulator to allow control of the solution flow rate; and
   (d) a central control unit electrically connected to said container and to at least one temperature sensor, which is arranged to regulate the power supplied to electrical resistors according to user data entered into said central control unit and signals received from the temperature sensor for heating said solution, which, in use, is fed into the patient through said needle.

2. The device according to claim 1 wherein said container provides a consistent heating of the heating pouch.

3. The device according to claim 1 wherein the dispensing of intravenous solutions is at a constant temperature of 36 degrees C., plus or minus 1 degree C.

4. The device according to claim 1 wherein said protracted thermal bag covering the catheter is equipped with electrical resistors electrically connected to and regulated by the central control unit, for the purpose of preventing heat losses along this catheter.

5. The device according to claim 1 wherein at least one temperature sensor is associated with a free end of the protracted thermal bag for monitoring the temperature of the intravenous solution at this point.

* * * * *